United States Patent [19]
Mathison et al.

[11] 3,947,454
[45] Mar. 30, 1976

[54] 5 OR 1'-HYDROXY-2-ALKYL-7,8-CYCLOPENTANO[h]-1,2,3,4-TETRAHYDROISOQUINOLINES AND ESTERS

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[22] Filed: Mar. 28, 1974

[21] Appl. No.: 455,672

[52] U.S. Cl.... 260/287 CF; 260/286 R; 260/286 Q; 260/287 D; 260/289 C; 260/289 K; 260/289 D; 424/258
[51] Int. Cl.$^2$................................ C07D 217/00
[58] Field of Search................ 260/287 R, 289 C

[56] References Cited
OTHER PUBLICATIONS

Morrison et al., "Organic Chemistry", 1966, pp. 314–315.
Marchant, "J. Chem. Soc.", 1956, p. 327ff.
March, "Advanced Organic Chemistry", 1968, p. 349.
Morrison and Boyd, "Organic Chemistry", 1966, p. 631.
Burger, "Medicinal Chemistry", pp. 42, 497.

*Primary Examiner*—Richard J. Gallagher
*Assistant Examiner*—David E. Wheeler
*Attorney, Agent, or Firm*—Merriam, Marshall, Shapiro & Klose

[57] ABSTRACT

5 or 1'-Hydroxy-2-alkyl-7,8-cyclopentano[h]-1,2,3,4-tetrahydroisoquinolines and esters of the formulas

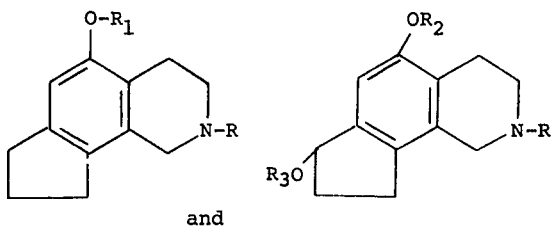

and wherein R is a lower alkyl having 1 to 6 carbon atoms, $R_1$ is hydrogen, a lower alkyl group, an alkanoyl, benzoyl or aralkanoyl group, $R_2$ is a lower alkyl group and $R_3$ is hydrogen, benzoyl, an alkanoyl group or an aralkanoyl group, and acid addition salts and quaternary ammonium salts thereof. The compounds are useful in pharmaceutical compositions for lowering blood pressure in animals.

11 Claims, No Drawings

5 OR 1'-HYDROXY-2-ALKYL-7,8-CYCLOPENTANO[H]-1,2,3,4-TETRAHYDROISOQUINOLINES AND ESTERS

This invention relates to novel chemical compounds and their production. More particularly, this invention provides novel tetrahydroisoquinolines processes for producing the compounds, novel intermediates useful in making the compounds, and novel pharmaceutical compositions containing the compounds useful for effecting desirable pharmacological activity in animals.

According to one aspect of the subject invention there is provided novel 5 or 1'-hydroxy-2-alkyl-7,8-cyclopentano[h]-1,2,3,4-tetrahydroisoquinolines and esters thereof of the formulas

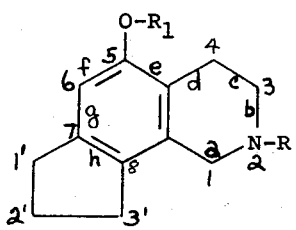

Formula 1

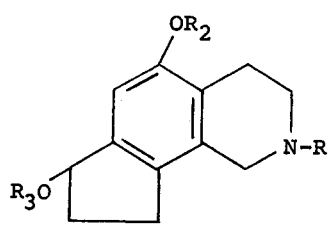

Formula 2 wherein R is a lower alkyl having 1 to 6 carbon atoms such as methyl, ethyl, isopropyl, butyl and n-hexyl, $R_1$ is hydrogen, a lower alkyl group such as defined for R, an alkanoyl group such as formyl, acetyl, propionyl, butyryl and octoyl, benzoyl and aralkanoyl groups such as phenylacetyl and phenylpropionyl, $R_2$ is a lower alkyl group such as defined for R, and $R_3$ is hydrogen, benzoyl or an alkanoyl or aralkanoyl group such as defined for $R_1$, and acid addition and quaternary ammonium salts thereof.

The compounds of Formula 1 are prepared by chemically reducing 5-alkoxy-2-alkyl-7,8-cyclopentano[h]-1,2,3,4-tetrahydroisoquinoline-1'-ones to 1'-hydroxy-5-alkoxy-2-alkyl-7,8-cyclopentano[h]-1,2,3,4-tetrahydroisoquinolines, hydrogenolyzing the said compounds to 5-alkoxy-2-alkyl-7,8-cyclopentano[h]-1,2,3,4-tetrahydroisoquinolines, then cleaving the ether group to form the corresponding 5-hydroxy-2-alkyl-7,8-cyclopentano[h]-1,2,3,4-tetrahydroisoquinolines and then esterifying the compounds. This process can be represented as follows:

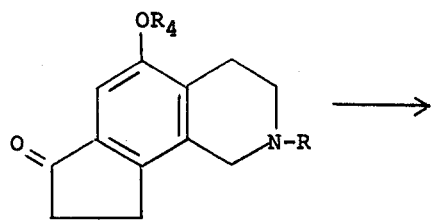

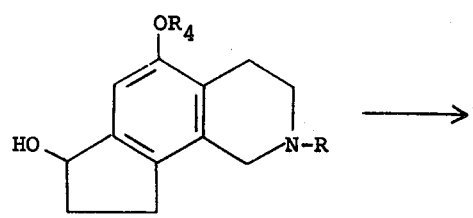

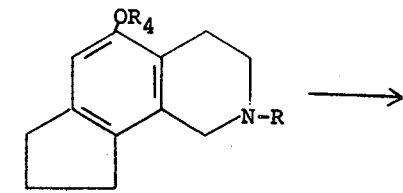

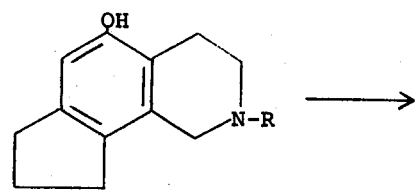

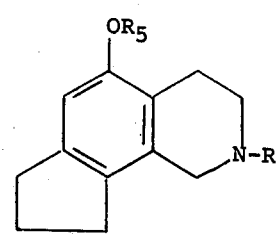

wherein R has the significance previously assigned, $R_4$ is a lower alkyl as defined for R, and $R_5$ is an alkanoyl, benzoyl or aralkanoyl group as defined for $R_1$.

Some of the 5-alkoxy-2-alkyl-7,8-cyclopentano[h]-1,2,3,4-tetrahydroisoquinoline-1'-ones which can be used as starting materials in this invention are 5-methoxy-2-methyl-7,8-cyclopentano[h]-1,2,3,4-tetrahydroisoquinoline-1'-one, 5-ethoxy-2-ethyl-7,8-cyclopentano[h]-1,2,3,4,-tetrahydroisoquinoline-1'-one, 5-propoxy-2-propyl-7,8-cyclopentano[h]-1,2,3,4-tetrahydroisoquinoline-1'-one and 5-methoxy-2-ethyl-7,8-cyclopentano[h]-1,2,3,4-tetrahydroisoquinoline-1'-one.

The 5-alkoxy-2-alkyl-7,8-cyclopentano[h]-1,2,3,4-tetrahydroisoquinoline-1'-ones can be readily reduced by use of lithium aluminum hydride in an inert liquid reaction medium, such as diethyl ether, at an elevated temperature, such as the reflux temperature. After the reaction is terminated, water can be added to the reaction mixture to decompose any excess hydride. The desired reaction product can be recovered by conventional methods.

Among the 1'-hydroxy-5-alkoxy-2-alkyl-7,8-cyclopentano[h]-1,2,3,4-tetrahydroisoquinolines which can be produced as described are 1'-hydroxy-5-methoxy-2-methyl-7,8-cyclopentano[h]-1,2,3,4-tetrahydroisoquinoline, 1'-hydroxy-5-ethoxy-2-ethyl-7,8-cyclopentano[h]-1,2,3,4-tetrahydroisoquinoline, 1'-hydroxy-5-propoxy-2-propyl-7,8-cyclopentano[h]-1,2,3,4-tetrahydroisoquinoline and 1'-hydroxy-5-methoxy-2-propyl-7,8-cyclopentano[h]-1,2,3,4-tetrahydroisoquinoline.

In the second step of the process the 1'-hydroxy-5-alkoxy-2-alkyl-7,8-cyclopentano[h]-1,2,3,4-tetrahydroisoquinoline is subjected to hydrogenolysis in a concentrated aqueous acid solution, such as concentrated hydrochloric acid, by contacting it with hydrogen at a moderately elevated pressure, such as in the range of 40 to 100 psig, in the presence of a suitable catalyst, such as palladium. Following termination of the reaction, sodium hydroxide or some other suitable base can be added to the reaction mixture until it is basic, after which the product can be extracted by use of a water insoluble solvent such as diethyl ether. The product can be separated from the solvent by evaporation of the solvent.

Representative of the 5-alkoxy-2-alkyl-7,8-cyclopentano[h]-1,2,3,4-tetrahydroisoquinolines which can be produced by the second step of the reaction are 5-methoxy-2-methyl-7,8-cyclopentano[h]-1,2,3,4-tetrahydroisoquinoline, 5-ethoxy-2-ethyl-7,8-cyclopentano[h]-1,2,3,4-tetrahydroisoquinoline, 5-propoxy-2-propyl-7,8-cyclopentano[h]-1,2,3,4-tetrahydroisoquinoline and 5-methoxy-2-propyl-7,8-cyclopentano[h]-1,2,3,4-tetrahydroisoquinoline.

Conversion of the 5-alkoxy-2-alkyl-7,8-cyclopentano[h]-1,2,3,4-tetrahydroisoquinolines to the corresponding 5-hydroxy compounds is effected by cleavage of the ether group using concentrated aqueous hydrobromic acid or hydriodic acid at reflux temperature. Following the reaction the desired product can be recovered by standard isolation techniques.

Some of the 5-hydroxy-2-alkyl-7,8-cyclopentano[h]-1,2,3,4-tetrahydroisoquinolines which are obtained as just described from the appropriate starting material are 5-hydroxy-2-methyl-7,8-cyclopentano[h]-1,2,3,4-tetrahydroisoquinoline, 5-hydroxy-2-ethyl-7,8-cyclopentano[h]-1,2,3,4-tetrahydroisoquinoline, 5-hydroxy-2-propyl-7,8-cyclopentano[h]-1,2,3,4-tetrahydroisoquinoline and 5-hydroxy-2-butyl-7,8-cyclopentano[h]-1,2,3,4-tetrahydroisoquinoline.

Esterification of the 5-hydroxy-2-alkyl-7,8-cyclopentano[h]-1,2,3,4-tetrahydroisoquinolines can be effected by contacting the hydroxy-containing compound with an alkanoic acid, benzoic acid or an aralkanoic acid in a suitable liquid reaction medium in the presence of N,N-carbonyldiimidazole. The reaction proceeds quickly at reflux temperature. Following termination of the reaction the product can be separated by standard procedures.

Some of the esters which can be produced, by use of the appropriate acid, are 5-(D,L-α-methylbutyryloxy)-2-methyl-7,8-cyclopentano[h]-1,2,3,4-tetrahydroisoquinoline, 5-formyloxy-2-methyl-7,8-cyclopentano[h]-1,2,3,4-tetrahydroisoquinoline, 5-acetoxy-2-ethyl-7,8-cyclopentano[h]-1,2,3,4-tetrahydroisoquinoline, 5-propionyloxy-2-propyl-7,8-cyclopentano[h]-1,2,3,4-tetrahydroisoquinoline, 5-benzoyloxy-2-methyl-7,8-cyclopentano[h]-1,2,3,4-tetrahydroisoquinoline and 5-phenylacetoxy-2-ethyl-7,8-cyclopentano[h]-1,2,3,4-tetrahydroisoquinoline.

Esters of the 1'-hydroxy compounds of Formula 2 can be readily prepared by esterification of the 5-alkoxy-2-alkyl-7,8-cyclopentano[h]-1,2,3,4-tetrahydroisoquinolines using the procedures just previously described for making esters. Some of the novel esters which can be produced from the appropriate acids and 1'-hydroxy compounds are 1'-cD,L-α-methylbutyryloxy)-5-methoxy-2-methyl-7,8-cyclopentano[h]-1,2,3,4-tetrahydroisoquinoline, 1'-formyloxy-5-methoxy-2-methyl-7,8-cyclopentano[h]-1,2,3,4-tetrahydroisoquinoline, 1'-acetoxy-5-ethoxy-2-ethyl-7,8-cyclopentano[h]-1,2,3,4-tetrahydroisoquinoline, 1'-propionyloxy-5-propoxy-2-propyl-7,8-cyclopentano[h]-1,2,3,4-tetrahydroisoquinoline, 1'-benzoyloxy-5-methoxy-2-methyl-7,8-cyclopentano[h]-1,2,3,4-tetrahydroisoquinoline and 1'-phenylacetoxy-5-ethoxy-2-ethyl-7,8-cyclopentano[h]-1,2,3,4-tetrahydroisoquinoline.

The compounds of this invention, being tertiary amines, can be converted to acid addition salts by contacting the amines with a suitable inorganic acid such as hydrochloric acid, sulfuric acid, phosphoric acid and hydrobromic acid or an organic acid such as citric acid, acetic acid, formic acid, malic acid, fumaric acid, succinic acid, benzoic acid and tartaric acid.

Quaternary ammonium salts of the compounds are readily prepared by contacting the compounds with an alkyl halide, alkyl sulfate, aralkyl halide or aralkyl sulfate such as methyl chloride, ethyl bromide, propyl iodide, benzyl chloride, benzyl sulfate and methyl sulfate as well as other compounds known to form quaternary ammonium salts with tertiary amines.

Since the compounds provided by this invention are amines they are useful as neutralizing agents since they form salts with acids. The amines can also be used in the isolation and purification of penicillin with which they form salts.

The compounds of this invention, particularly in the form of the free bases and the nontoxic acid addition salts, are also useful pharmaceutically. These compounds when administered to animals intraperitoneally or orally exert an anti-hypertensive effect. The compounds thus can be used to reduce blood pressure.

1'-Hydroxy-5-methoxy-2-methyl-7,8-cyclopentano[h]-1,2,3,4-tetrahydroisoquinoline has an $ALD_{50}$ in mice of 16 mg./kg. i.p. when administered in solution prepared with the acid of dilute acid. When administered as the base at 4 mg./kg. i.p. in solution, prepared with the aid of dilute acid, to hypertensive rats the following percent change in systolic blood pressure was observed:

| 1 Hour | −3.1 ± 1.0 |
| 2 Hours | −2.3 ± 1.2 |
| 4 Hours | −4.9 ± 1.4 |
| 24 Hours | −0.4 ± 1.4 |

5-Methoxy-2-methyl-7,8-cyclopentano[h]-1,2,3,4-tetrahydroisoquinoline as the base has an $ALD_{50}$ in mice of 100–150 mg./kg. i.p. when administered in distilled water. When administered as the base in distilled water at 50 mg./kg. i.p. to hypertensive rats the following percent change in systolic blood pressure was observed:

| 1 Hour | −3.0 ± 5.5 |
| 2 Hours | −2.9 ± 2.4 |
| 4 Hours | −6.3 ± 2.2 |
| 24 Hours | −4.6 ± 2.7 |

5-Hydroxy-2-methyl-7,8-cyclopentano[h]-1,2,3,4-tetrahydroisoquinoline as the base administered as a solution in distilled water has an $ALD_{50}$ in mice of 100–150 mg./kg. i.p. When administered as the base, as a solution in distilled water, at 50 mg./kg. i.p. to hypertensive rats the following change in systolic blood pressure was observed:

| 1 Hour | −18.9 ± 2.8 |
| 2 Hours | −13.6 ± 3.6 |
| 4 Hours | −11.2 ± 2.6 |
| 24 Hours | − 4.7 ± 4.0 |

5-(D,L-α-Methylproionyloxy)-2-methyl-7,8-cyclopentano[h]-1,2,3,4-tetrahydroisoquinoline as the base administered as a solution in distilled water has an $ALD_{50}$ in mice of 100–150 mg./kg. i.p. When administered as the base, as a solution in distilled water, at 25 mg./kg. i.p. to hypertensive rats the following change in systolic blood pressure was observed:

| 1 Hour | −15.3 ± 1.8 |
| 2 Hours | −13.6 ± 2.5 |
| 4 Hours | −15.4 ± 4.9 |
| 24 Hours | −10.8 ± 2.4 |

At a dose of 50 mg./kg. i.p. the same compound reduced the systolic blood pressure in hypertensive rats as follows:

| 1 Hour | −23.5 ± 4.3 |
| 2 Hours | −26.2 ± 1.6 |
| 4 Hours | −15.8 ± 1.9 |
| 24 Hours | −10.2 ± 2.6 |

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

| | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 5-Hydroxy-2-methyl-7,8-cyclopentano[h]-1,2,3,4-tetrahydroisoquinoline.

Since the compounds exhibit both oral and parenteral activity they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art, such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

The 5-alkoxy-2-alkyl-7,8-cyclopentano[h]-1,2,3,4-tetrahydroisoquinoline-1′-ones used as starting materials in this invention can be produced by converting a 5-alkoxy-2-alkyl-1,2,3,4-tetrahydroisoquinoline by means of a Friedel-Crafts reaction to a 5-alkoxy-2-alkyl-1,2,3,4-tetrahydroisoquinoline-8-carboxaldehyde, reacting the aldehyde with malonic acid to form a β-(5-alkoxy-2-alkyl-1,2,3,4-tetrahydroisoquinoline-8)propenoic acid, catalytically reducing the propenoic acid compound to form the β-(5-alkoxy-2-alkyl-1,2,3,4-tetrahydroisoquinoline-8)propanoic acid and then effecting ring closure of such compound, such as by means of polyphosphoric acid. This process can be represented as follows:

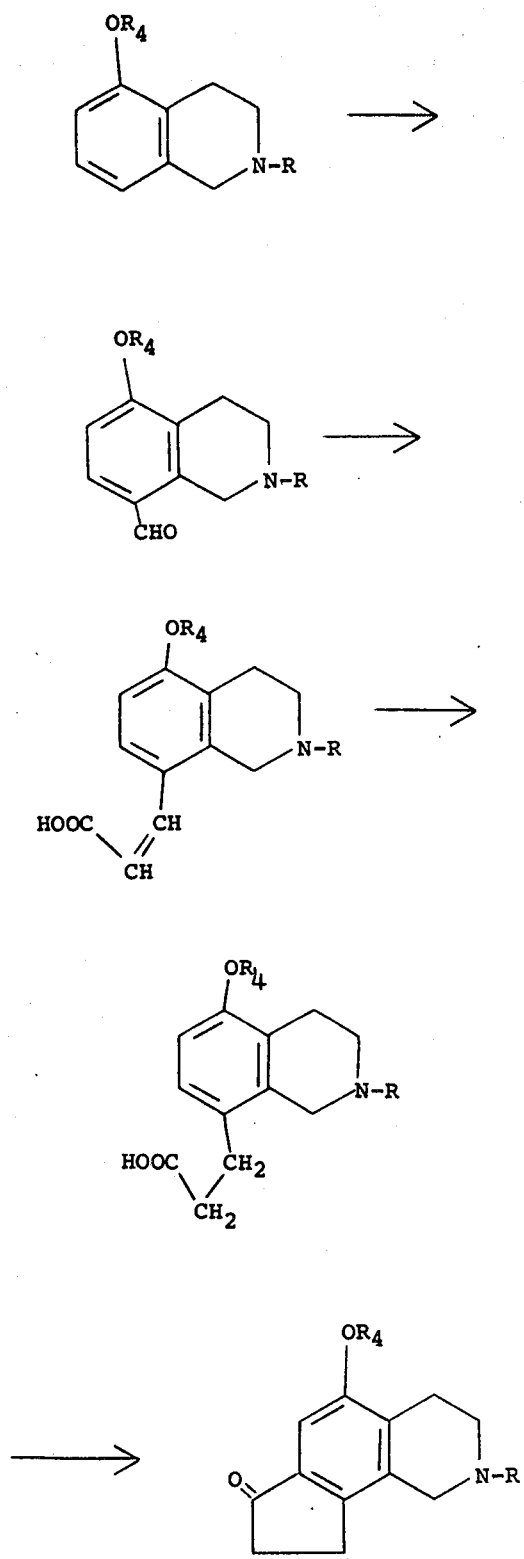

wherein R and R₄ are the same or different lower alkyl groups having 1 to 6 carbon atoms. Durand et al., *Bull. Soc. Chem. France*, 270 (1961) discloses the preparation of 5-methoxy-2-methyl-1,2,3,4-tetrahydroisoquinoline. Other such compounds can be prepared by the same process from the appropriate reactants. In addition, the preparation of the starting materials is well within the ordinary skill of an organic chemist. Examples 6 to 9 illustrate specifically the preparation of one such starting material by the described process.

EXAMPLE 1

1′-Hydroxy-5-methoxy-2-methyl-7,8-cyclopentano[h]-1,2,3,4-tetrahydroisoquinoline Into a flask (1 liter) equipped with a mechanical stirrer, an equilibrium addition funnel (500 ml.), and a condenser fitted with a calcium chloride drying tube was placed lithium aluminum hydride (0.72 g., 0.0190 mole) which was covered with anhydrous diethyl ether (150 ml.). The contents of the flask were cooled to 0°C. and stirred while an anhydrous diethyl ether solution (300 ml.) of 5-methoxy-2-methyl-7,8-cyclopentano[h]-1,2,3,4-tetrahydroisoquinoline-1′-one (2.20 g., 0.0095 mole) was added dropwise rapidly. When the addition was complete, the reaction mixture was allowed to warm to room temperature, then refluxed for 5 hrs. To destroy excess hydride, the following steps were taken: the contents of the flask were cooled to 0°C., diatomaceous earth filter-aid (1.5 g.) was added, and ice cold water was added very slowly until the reaction mixture lost its gray color. The ether solution was then decanted and dried over sodium sulfate. Removal of the ether afforded the crude product 1′-hydroxy-5-methoxy-2-methyl-7,8-cyclopentano[h]-1,2,3,4-tetrahydroisoquinoline which was recrystallized from diethyl ether, m.p. 112.5°–113.5°C. (1.95 g., 84%).

EXAMPLE 2

5-Methoxy-2-methyl-7,8-cyclopentano[h]-1,2,3,4-tetrahydroisoquinoline

Into an hydrogenation bottle (500 ml.) filled with nitrogen were placed 5% palladium on charcoal (0.4 g.) and a solution consisting of 1′-hydroxy-5-methoxy-2-methyl-7,8-cyclopentano[h]-1,2,3,4-tetrahydroisoquinoline (1.4 g., 0.0061 mole) and ethanol (200 ml.) to which had previously been added concentrated hydrochloric acid (2 ml.). Hydrogenolysis occurred during a 48 hr. period in contact with hydrogen in a low pressure hydrogenation apparatus. After collection of the catalyst by filtration, the filtrate was made basic with sodium hydroxide (10%). The precipitated sodium chloride was collected by filtration and the filtrate was poured into a flask (500 ml.) from which the solvent was removed on an evaporator. Diethyl ether (200 ml.) was added to the cooled residue. After thorough agitation of the residue in the ether, the undissolved sodium chloride was collected by filtration and the filtrate was dried over sodium sulfate. Removal of the ether afforded the product 5-methoxy-2-methyl-7,8-cyclopentano[h]-1,2,3,4-tetrahydroisoquinoline, m.p. 78°–80°C. (1.30 g., 98%). The product was further purified by preparing its hydrobromide salt, which was recrystallized from ethanol, m.p. 244°–245°C.

EXAMPLE 3

5-Hydroxy-2-methyl-7,8-cyclopentano[h]-1,2,3,4-tetrahydroisoquinoline hydrobromide A suspension of the hydrobromide of 5-methoxy-2-methyl-7,8-cyclopentano[h]-1,2,3,4-tetrahydroisoquinoline (2.0 g., 0.0066 mole) in hydrobromic acid (48%, 25 ml.) was gently refluxed for 3 hours. The excess HBr was removed on a solvent evaporator and the residue was recrystallized from acetonitrile affording the pure product 5-hydroxy-2-methyl-7,8-cyclopentano[h]-1,2,3,4-tetrahydroisoquinoline HBr, m.p. 265°–267°C. (1.1 g., 58%).

EXAMPLE 4

5-(D,L-α-Methylbutyryloxy)-2-methyl-7,8-cyclopentano[h]-1,2,3,4-tetrahydroisoquinoline hydrobromide D,L-α-methylbutyric acid was prepared by basic hydrolysis of the corresponding acid chloride, acidification of the reaction mixture, isolation by ether extraction, and purification by vacuum distillation (b.p. 82°–84°C./20 mm.).

N,N-Carbonyldiimidazole (0.28 g., 0.00172 mole), D,L-α-methylbutyric acid (0.18 g., 0.0019 mole), and tetrahydrofuran (65 ml.) were placed in a flask and the solution was refluxed for 15 min. After cooling, 5-hydroxy-2-methyl-7,8-cyclopentano[h]-1,2,3,4-tetrahydroisoquinoline (0.35 g., 0.00172 mole) was added and the solution was refluxed for 2 hrs. The solvent was removed and the residue was dissolved in chloroform and extracted twice with sodium bicarbonate (2%, 200 ml. portions) and twice with water (200 ml.). The chloroform layer was dried over sodium sulfate, the chloroform was removed, and the residue was dissolved in ether. Hydrogen bromide gas was bubbled into the stirred ether solution and the product 5-(D,L-α-methylbutyryloxy)-2-methyl-7,8-cyclopentano[h]-1,2,3,4-tetrahydroisoquinoline hydrobromide was collected by filtration and purified by recrystallization from ethyl acetate, m.p. 184°–195°C. (0.46 g., 71%).

EXAMPLE 5

1'-(D,L-α-methylbutyryloxy)-5-methoxy-2-methyl-7,8-cyclopentano[h]-1,2,3,4-tetrahydroisoquinoline Into a flask were placed N,N-carbonyldiimidazole (0.69 g., 0.0042 mole), D,L-α-methylbutyric acid (0.46 g., 0.0045 mole) and tetrahydrofuran (60 ml.) and the solution was refluxed for 15 min. After cooling, 1'-hydroxy-5-methoxy-2-methyl-7,8-cyclopentano[h]-1,2,3,4-tetrahydroisoquinoline (1.0 g., 0.0042 mole) was added and the solution was refluxed for 2 hrs. The solvent was removed and the residue was dissolved in chloroform and extracted twice with sodium bicarbonate (2%, 200 ml. portions) and water (200 ml.). The chloroform layer was dried over sodium sulfate, the solvent was removed, and the residue was dissolved in ethanol (3 ml.) and chromatographed on silica gel (13 in. × 1 in. column) with ethanol. The purified product was a thick viscous oil (0.57 g., 42%) which partially solidified (m.p. 62°–64°C.) after standing under nitrogen for 10 days.

EXAMPLE 6

5-Methoxy-2-methyl-1,2,3,4-tetrahydroisoquinoline-8-carboxaldehyde

Into a flask equipped with a mechanical stirrer, an equilibrium addition funnel, and a condenser fitted with a calcium chloride drying tube, were placed methylene chloride (150 ml.) and 5-methoxy-2-methyl-1,2,3,4-tetrahydroisoquinoline (15.0 g., 0.085 mole). The solution was cooled to 0°C. and stirred. Titanium tetrachloride (51.6 g., 0.272 mole) was added gradually, followed by the rapid dropwise addition of α,α-dichloromethyl methyl ether (9.8 g., 0.085 mole). After the reaction mixture was allowed to warm to room temperature, it was refluxed for 7 hrs. The titanium chloride complex of the product was decomposed with water and ice, and the resulting solution kept cool as it was made basic with excess sodium hydroxide (20%). The resulting suspension was extracted with chloroform. The extract was dried over sodium sulfate and the solvent removed, affording the crude product which was vacuum distilled (b.p. 122°C./0.1 mm.) to yield 13.0 g. (74%) of 5-methoxy-2-methyl-1,2,3,4-tetrahydroisoquinoline-8-carboxaldehyde. The hydrochloride salt melted at 244°–245°C. after recrystallization from absolute ethanol.

EXAMPLE 7

β-(5-Methoxy-2-methyl-1,2,3,4-tetrahydroisoquinoline-8)propenoic acid hydrochloride Into a flask (100 ml.) were placed malonic acid (12.0 g., 0.116 mole) and dry pyridine (25 ml.). The contents of the flask were heated until solution occurred. After the solution had cooled to room temperature, 5-methoxy-2-methyl-1,2,3,4-tetrahydroisoquinoline-8-carboxaldehyde (12.0 g., 0.058 mole) was added. Piperidine (25 drops) was added as a catalyst. The reaction mixture was warmed for 30 min. at 80°C. followed by a 2½ hr. refluxing. After the solution had cooled, it was poured into cold water (200 ml.) and the precipitate was collected by filtration and dried (4 hrs., 110°C.); it was then ground and further dried (2 hrs., 110°C.) in a vacuum oven. The filtrate was successively concentrated and cooled until no additional product precipitated. The β-(5-methoxy-2-methyl-1,2,3,4-tetrahydroisoquinoline-8)propenoic acid hydrochloride, m.p. 260°–265°C. (11.5 g., 70%) was not purified.

EXAMPLE 8

β-(5-Methoxy-2-methyl-1,2,3,4-tetrahydroisoquinoline-8)propanoic acid hydrochloride Into a hydrogenation bottle (500 ml.) were placed 5% palladium on charcoal (0.5 g.) and a suspension of β-(5-methoxy-2-methyl-1,2,3,4-tetrahydroisoquinoline-8)propenoic acid HCl (5.7 g., 0.028 mole) in dilute (1%) hydrochloric acid (250 ml.). The compound was reduced with hydrogen during a 20 hr. period in a low pressure hydrogenation apparatus. After removal of the catalyst by filtration, the filtrate was successively concentrated and cooled until no further product precipitated. The portions of the product β-(5-methoxy-2-methyl-1,2,3,4-tetrahydroisoquinoline-8)propanic acid hydrochloride were collected by filtration and dried (4 hrs., 110°C.) in a vacuum oven. If the dry product (4.8 g., 84%) had a melting point less than 210°C., it was recrystallized from water (m.p. 212°C.).

EXAMPLE 9

5-Methoxy-2-methyl-7,8-cyclopentano[h]-1,2,3,4-tetrahydroisoquinoline-1'-one

Into a flask (500 ml.) which was heated to 55°C. with an oil bath and equipped with a mechanical stirrer, calcium chloride drying tube, and a thermometer, were placed preheated (steam bath) polyphosphoric acid (PPA) (100 g.) and β-(5-methoxy-2-methyl-1,2,3,4-tetrahydroisoquinoline-8)propanoic acid (7.4 g., 0.026 mole). The mixture was stirred as the temperature of the oil bath was gradually raised. At an internal temperature of 60°C. the reaction commenced, as evidenced by a light green color. The internal temperature was raised to 78°C. over a 15 min. period and maintained there for a further 20 min. The reaction mixture became dark green during this time. The PPA complex formed was then decomposed with ice and water after the contents of the flask had cooled to room temperature. The solution was kept at room temperature or cooler during basification with sodium hydroxide (20%) by the addition of large amounts of ice. The resulting suspension was extracted with diethyl ether and the extract was dried over sodium sulfate. Removal of the ether afforded the crude product 5-methoxy-2-methyl-7,8-cyclopentano[h]-1,2,3,4-tetrahydroisoquinoline-1'-one which was recrystallized (m.p. 151°–152°C.) from diethyl ether (3.9 g., 65%).

The foregoing detailed description has been given for clearness of understanding only, and no unnecessary limitations should be understood therefrom, as modifications will be obvious to those skilled in the art.

What is claimed is:

1. A compound of the formulas

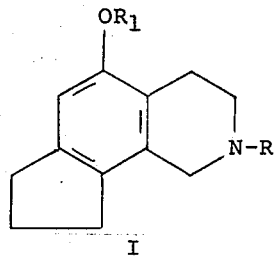

I and

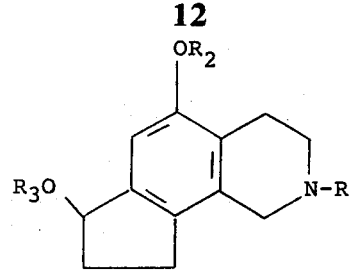

II wherein R is a lower alkyl having 1 to 6 carbon atoms, $R_1$ is hydrogen, a lower alkyl having 1 to 6 carbon atoms, an alkanoyl having 1 to 8 carbon atoms, benzoyl or a phenyl-lower alkanoyl in which the alkanoyl has 1 to 8 carbon atoms, $R_2$ is a lower alkyl group having 1 to 6 carbon atoms and $R_3$ is hydrogen, benzoyl, an alkanoyl having 1 to 8 carbon atoms or a phenyl-lower alkanoyl in which the alkanoyl has 1 to 8 carbon atoms, and non-toxic acid addition salts thereof.

2. A compound according to formula I of claim 1 in which $R_1$ is alkyl.

3. A compound according to formula I of claim 1 in which $R_1$ is alkanoyl.

4. A compound according to claim 3 in which R is methyl and $R_1$ is α-methylbutyryl.

5. A compound according to claim 2 in which R is methyl and $R_1$ is methyl.

6. A compound according to formula I of claim 1 in which $R_1$ is hydrogen.

7. A compound according to claim 6 in which R is methyl.

8. A compound according to formula II of claim 1 in which $R_3$ is hydrogen.

9. A compound according to claim 8 in which R and $R_2$ are each methyl.

10. A compound according to formula II of claim 1 in which $R_3$ is alkanoyl.

11. A compound according to claim 10 in which R and $R_2$ are each methyl and $R_3$ is α-methylbutyryl.

* * * * *

UNITED STATES PATENT AND TRADEMARK OFFICE
CERTIFICATE OF CORRECTION

PATENT NO. : 3,947,454
DATED : March 30, 1976
INVENTOR(S) : Ian William Mathison et al.

It is certified that error appears in the above-identified patent and that said Letters Patent are hereby corrected as shown below:

Column 1, line 9, insert a comma (,) after "tetrahydroisoquinolines"; line 53, "R," should be --$R_1$--; Column 3, line 2, "R," should be --$R_1$--; Column 4, line 30, "-cD,L-" should be -- -(D,L- --; Column 5, line 2, "acid" should be --aid--; line 39, "-Methylproionyloxy)-" should be -- -Methylpropionyloxy--.

Signed and Sealed this eighth Day of June 1976

[SEAL]

Attest:

RUTH C. MASON
Attesting Officer

C. MARSHALL DANN
Commissioner of Patents and Trademarks